United States Patent
Tsuda et al.

(10) Patent No.: US 10,132,778 B2
(45) Date of Patent: Nov. 20, 2018

(54) FIBER WAVINESS DETECTION METHOD AND APPARATUS FOR CONDUCTIVE COMPOSITE MATERIALS

(71) Applicant: IHI CORPORATION, Koto-ku (JP)

(72) Inventors: Akinori Tsuda, Koto-ku (JP); Hiroaki Hatanaka, Koto-ku (JP); Shinji Muto, Koto-ku (JP); Koichi Inagaki, Koto-ku (JP); Hiroyuki Hishida, Koto-ku (JP); Akiyoshi Sato, Koto-ku (JP)

(73) Assignee: IHI Corporation, Koto-ku (JP)

( * ) Notice: Subject to any disclaimer, the term of this patent is extended or adjusted under 35 U.S.C. 154(b) by 268 days.

(21) Appl. No.: 15/085,525

(22) Filed: Mar. 30, 2016

(65) Prior Publication Data
US 2016/0209365 A1 Jul. 21, 2016

Related U.S. Application Data

(63) Continuation of application No. PCT/JP2014/065605, filed on Jun. 12, 2014.

(30) Foreign Application Priority Data

Oct. 11, 2013 (JP) ................................. 2013-213393

(51) Int. Cl.
*G01N 27/72* (2006.01)
*G01N 27/82* (2006.01)
(Continued)

(52) U.S. Cl.
CPC ............ *G01N 27/72* (2013.01); *B29C 70/30* (2013.01); *G01B 7/34* (2013.01); *G01B 7/345* (2013.01);
(Continued)

(58) Field of Classification Search
CPC .................................................... G01N 27/72
See application file for complete search history.

(56) References Cited

U.S. PATENT DOCUMENTS

| 4,763,071 A | 8/1988 | McGee et al. |
| 5,610,517 A | 3/1997 | Ma et al. |

(Continued)

FOREIGN PATENT DOCUMENTS

| CN | 101813655 | 8/2010 |
| JP | 2-150765 | 6/1990 |

(Continued)

OTHER PUBLICATIONS

International Search Report dated Jul. 8, 2014 in PCT/JP2014/065605, filed on Jun. 12, 2014(with English Translation).

(Continued)

*Primary Examiner* — Clayton E Laballe
*Assistant Examiner* — Jas Sanghera
(74) *Attorney, Agent, or Firm* — Oblon, McClelland, Maier & Neustadt, L.L.P.

(57) ABSTRACT

A pair of electrodes is connected to a test specimen in order to apply an electric current to the test specimen in the direction of a conductive fiber of each conductive fiber woven fabric of a plurality of prepregs as targets for verification of the presence or absence of waviness, among a plurality of prepregs constituting the test specimen composed of a conductive composite material, and then a magnetic field sensor is relatively scanned over the test specimen, while applying an electric current between the pair of electrodes, to determine a portion of the test specimen where a magnetic field variation is detected by the scanning of the magnetic field sensor as a portion where waviness of the conductive fibers of the conductive fiber woven fabric of the plurality of prepregs as targets for verification of the presence or absence of waviness is present. Thus, it is possible to grasp, for example, the condition of fibers of the conductive composite material in the test specimen as a whole.

3 Claims, 8 Drawing Sheets

(51) Int. Cl.
*B29C 70/30* (2006.01)
*G01B 7/34* (2006.01)
*G01N 33/36* (2006.01)
*G01M 5/00* (2006.01)

(52) U.S. Cl.
CPC .......... *G01M 5/0091* (2013.01); *G01N 27/82* (2013.01); *G01N 33/367* (2013.01)

(56) References Cited

U.S. PATENT DOCUMENTS

2008/0174306 A1 7/2008 Brady
2016/0009054 A1* 1/2016 Okunaka .................. C08J 5/042
　　　　　　　　　　　　　　　　　　　　　　428/113

FOREIGN PATENT DOCUMENTS

| JP | 5-269874 | 10/1993 |
| JP | 7-167839 | 7/1995 |
| JP | 2001-318070 | 11/2001 |
| JP | 2002-214201 | 7/2002 |
| JP | 2004-45145 A | 2/2004 |
| JP | 2007-327924 A | 12/2007 |
| JP | 2013-53858 | 3/2013 |

OTHER PUBLICATIONS

Extended European Search Report dated May 11, 2017 in Patent Application No. 14853037.1.

* cited by examiner

FIBER WAVINESS DETECTION METHOD AND APPARATUS FOR CONDUCTIVE COMPOSITE MATERIALS

TECHNICAL FIELD

Embodiments described herein relate to a fiber waviness detection method and apparatus for conductive composite materials used to detect waviness of conductive fibers of conductive fiber woven fabrics constituting a conductive composite material composed by laminating a plurality of prepregs prepared by impregnating the conductive fiber woven fabrics with resin.

BACKGROUND ART

A molding method using an autoclave has already been established in a case where a CFRP (conductive composite material) is molded by laminating a plurality of prepregs in which conductive fiber woven fabrics, for example, carbon-fiber woven fabrics are impregnated with thermosetting resin. Meanwhile, a molding method, for example, a mold press molding method, alternative to this molding method using an autoclave, is being built recently.

Waviness of carbon fibers that may affect mechanical properties of CFRPs needs to be newly verified for CFRPs molded by a molding method alternative to such a molding method using an autoclave as described above.

For example, assume that a direction along a plane of a test specimen is an in-plane direction and that a laminating direction of prepregs of the test specimen is an out-of-plane direction in a case where the presence or absence of waviness of carbon fibers is examined in the test specimen of CFRP molded into a cuboid by a mold press molding method. Then, in a conventional ultrasonic flaw detection test (see, for example, Patent Document 1), it is possible to detect a condition of carbon fiber waviness in the out-of-plane direction. It is not possible, however, to grasp a condition of carbon fiber waviness in the in-plane direction.

Accordingly, as it stands now, a cutting plane of the CFRP test specimen is observed to verify whether or not fiber waviness is present in this cutting plane or in the vicinity thereof. Alternatively, an X-ray CT inspection is performed on small cut pieces of the CFRP test specimen to examine each cut piece for the presence or absence of waviness of carbon fibers.

BACKGROUND ART DOCUMENT

Patent Document

Patent Document 1: Japanese Patent Laid-Open No. 02-150765

SUMMARY

Technical Problem

However, observation of a cutting plane of the above-described CFRP test specimen only provides information on the cutting plane or the vicinity thereof. It is therefore not possible to grasp a condition of fibers in the test specimen as a whole. The CFRP test specimen has to be cut into small pieces when performing an X-ray CT inspection. Accordingly, the X-ray CT inspection also has a problem of being not possible to grasp a condition of fibers in the test specimen as a whole, as in the case of cutting-plane observation. Solving this problem has therefore been a conventional task.

An object of the present disclosure, which has been made with a focus on the above-described conventional task, is to provide a fiber waviness detection method and apparatus for conductive composite materials capable of detecting fiber waviness without having to partially or finely cut a conductive composite material at the time of verifying the presence or absence of fiber waviness in the conductive composite material, thus enabling grasping of, for example, a condition of fibers of the conductive composite material in a test specimen as a whole.

Solution to Problem

The present inventors have paid attention to the electrical conductivity of conductive fiber woven fabrics constituting a conductive composite material and have conceived of applying an electric current to the conductive fibers of conductive fiber woven fabrics. Then, the inventors have found that when an electric current is applied in the direction of conductive fibers for which the presence or absence of waviness needs to be confirmed, a disturbance of magnetic fluxes arising in a portion of the conductive fibers where waviness in an in-plane fiber direction is present can be detected with a magnetic field sensor, and have thus developed the present disclosure.

A first aspect of the present disclosure is a fiber waviness detection method for conductive composite materials used to detect waviness of conductive fibers of conductive fiber woven fabrics constituting a conductive composite material composed by laminating a plurality of prepregs prepared by impregnating the conductive fiber woven fabrics with resin, wherein a pair of electrodes is connected to the conductive composite material, in order to apply an electric current to the conductive composite material in the direction of the conductive fibers of the conductive fiber woven fabrics of a plurality of prepregs as targets for verification of the presence or absence of waviness, among the plurality of prepregs constituting the conductive composite material, and then a magnetic field detection means is relatively scanned over the conductive composite material, while applying an electric current between the pair of electrodes, to determine a portion of the conductive composite material where a magnetic field variation is detected by the scanning of the magnetic field detection means as a portion where waviness is present in the conductive fibers of the conductive fiber woven fabrics of the plurality of prepregs as targets for verification of the presence or absence of waviness.

In the fiber waviness detection method for conductive composite materials according to the present disclosure, the conductive composite material as a target for detection of fiber waviness may be, for example, a conductive composite material in which carbon fibers are used for conductive fibers as the base material of conductive fiber woven fabrics, though the conductive composite material is not limited to this example.

At this time, thermoplastic resin or thermosetting resin is used for resin serving as the matrix of conductive fiber woven fabrics. As the thermoplastic resin, PEEK (polyether ether ketone resin), PEI (polyetherimide resin), or PIXA (thermoplastic polyimide resin), for example, is used. As the thermosetting resin, epoxy resin, PETI-5 or PMR-15, for example, is used.

In the fiber waviness detection method for conductive composite materials according to the present disclosure, when an electric current is applied between the pair of electrodes connected to the conductive composite material, the electric current flows in the direction of conductive fibers of conductive fiber woven fabrics of the plurality of prepregs as targets for verification of the presence or absence of waviness.

Then, the magnetic field detection means is relatively scanned over the conductive composite material under this condition to determine a portion of the conductive composite material where a magnetic field variation is detected by the magnetic field detection means as a portion where waviness is present in the conductive fibers of the plurality of prepregs as targets for verification of the presence or absence of waviness. It is therefore possible to detect fiber waviness without having to partially or finely cut, for example, a test specimen composed of the conductive composite material.

Advantageous Effects

In the fiber waviness detection method for conductive composite materials according to the present disclosure, it is possible to detect fiber waviness without having to partially or finely cut the conductive composite material at the time of verifying the presence or absence of fiber waviness in the conductive composite material. Accordingly, the method provides for the extremely beneficial effect of being able to grasp, for example, the condition of fibers of the conductive composite material in the test specimen as a whole.

DESCRIPTION OF EMBODIMENTS

Hereinafter, the present disclosure will be described according to the accompanying drawings.

FIGS. 1A to 4C illustrate one embodiment of a fiber waviness detection method and apparatus for conductive composite materials according to the present disclosure.

Figure 1A:
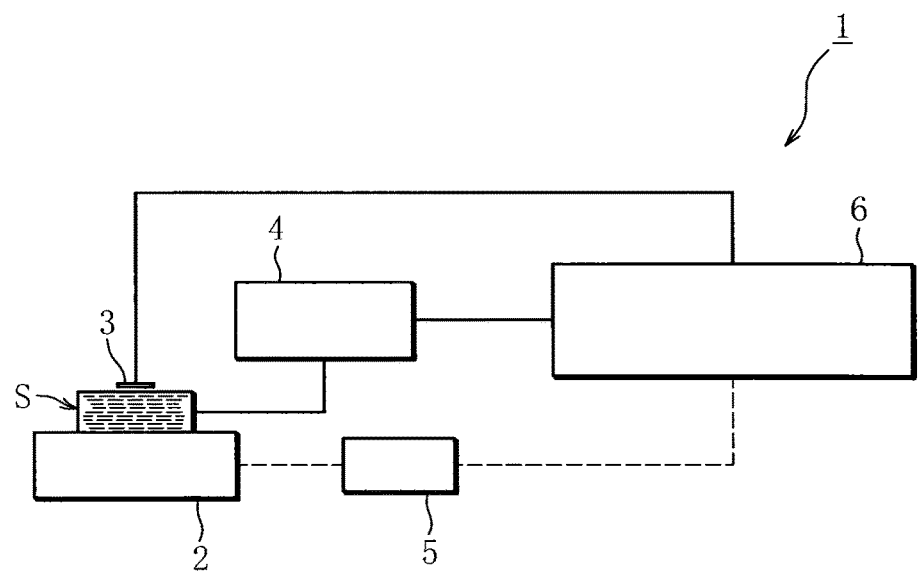
FIG. 1A is an explanatory view of the schematic configuration of a fiber waviness detection apparatus for conductive composite materials according to one embodiment of the present disclosure.

As illustrated in FIG. 1A, this fiber waviness detection apparatus 1 comprises a stage 2 on which a test specimen S of a conductive composite material is mounted; a magnetic field sensor (magnetic field detection means) 3 held above the test specimen S on the stage 2 with an appropriate space from the test specimen; a current-applying unit 4 for applying an electric current to the test specimen S as will be described later; a driver 5 for driving the stage 2; and a control unit 6. The test specimen S is electrified by the current-applying unit 4 according to a command from this control unit 6 and the stage 2 is driven likewise according to a command from the control unit 6 to the driver 5, thereby scanning the magnetic field sensor 3 over the test specimen S.

Figure 1B:
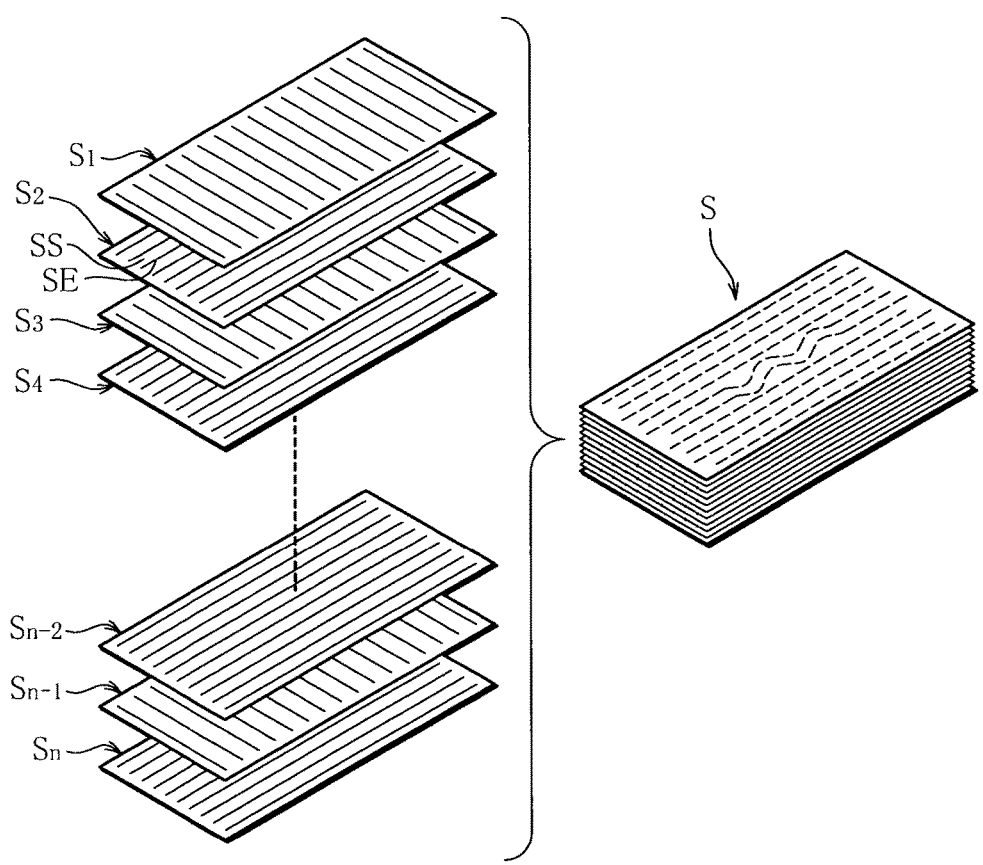
FIG. 1B is an explanatory perspective view illustrating a test specimen of a conductive composite material.

In this case, the test specimen S is formed into a cuboid by alternately laminating pluralities of prepregs ($S_1$, $S_3$, ..., $S_{n-1}$) and ($S_2$, $S_4$, ..., $S_n$) prepared by impregnating conductive fiber woven fabrics SS with thermoplastic resin or thermosetting resin and different from each other by 90° in fiber orientation direction, as illustrated in FIG. 1B. In this embodiment, a pair of electrodes 11 and 12 is connected to both ends of the test specimen S, as illustrated in FIG. 2A, in order to apply an electric current in the direction of a conductive fiber SE (longitudinal direction of FIG. 1B) of each conductive fiber woven fabric SS of a plurality of prepregs $S_2$, $S_4$, ..., $S_n$ as targets for verification of the presence or absence of waviness, among the plurality of prepregs $S_1$ to $S_n$ of the test specimen S.

Note that if the plurality of prepregs $S_1$, $S_3$, ..., $S_{n-1}$ is specified as the targets for the verification of the presence or absence of waviness, the pair of electrodes 11 and 12 is connected to both sides of the test specimen S, in order to apply an electric current in the direction of the conductive fiber SE (direction orthogonal to the longitudinal direction of FIG. 1B) of each conductive fiber woven fabric SS.

When the presence or absence of waviness of the conductive fiber SE of the test specimen S is verified using this fiber waviness detection apparatus 1, an electric current is first applied between the pair of electrodes 11 and 12 connected to the test specimen S using the current-applying unit 4. Consequently, an electric current flows in the direction of the conductive fiber SE (in the direction of an outline arrow in FIG. 2A) of each conductive fiber woven fabric SS of the plurality of prepregs $S_2$, $S_4$, ..., $S_n$ as targets for verification of the presence or absence of waviness.

Figure 2A:
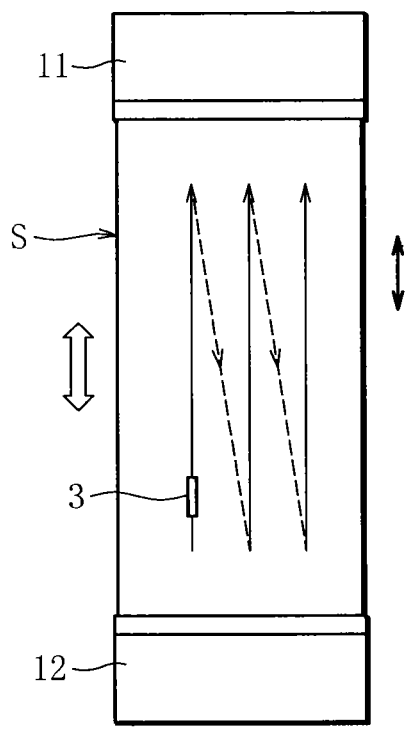
FIG. 2A is an explanatory plan view of a test specimen, illustrating a procedure of scanning by a magnetic field sensor of the fiber waviness detection apparatus for conductive composite materials illustrated in FIG. 1A.
Figure 2B:
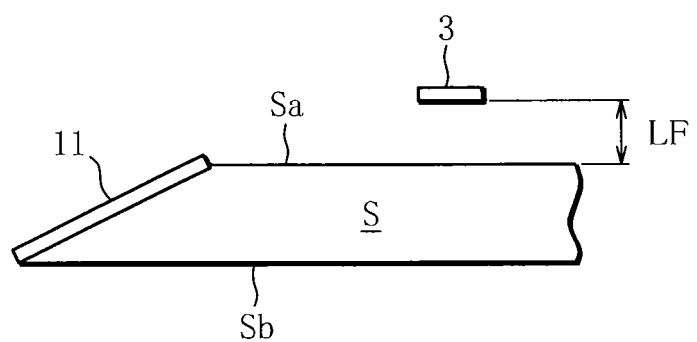
FIG. 2B is a partial side view of a test specimen, illustrating the positional relationship between the test specimen and a magnetic field sensor during scanning by a magnetic field sensor.

The stage 2 mounted with the test specimen S is actuated under this condition to scan the magnetic field sensor 3, whose direction of magnetic field detection is aligned with the direction of the thick arrow in FIG. 2A, over the test specimen S along the direction of the arrow. At this time, the magnetic field sensor 3 is scanned at a distance LF from the test specimen S (with the amount of liftoff LF), as illustrated in FIG. 2B.

Figure 3A:
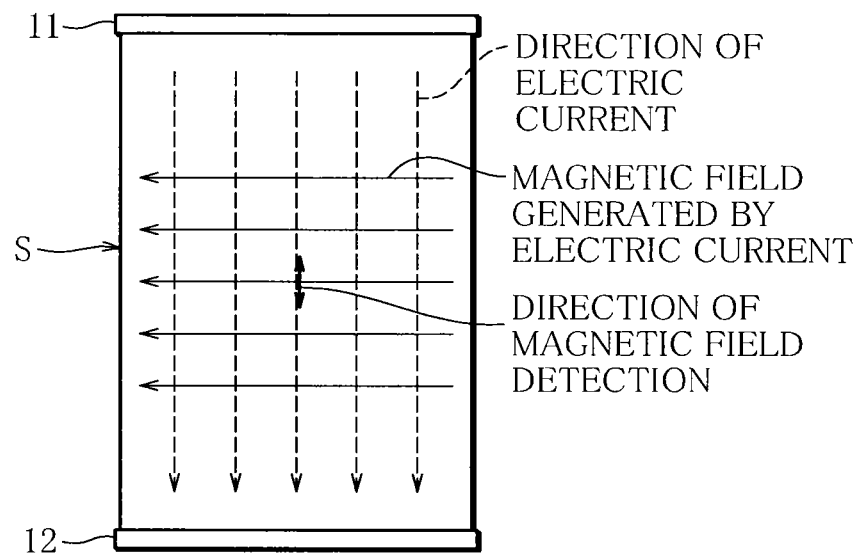
FIG. 3A is an explanatory view illustrating a magnetic field when no waviness is present in a case where scanning is performed using the magnetic field sensor shown in FIG. 2A.
Figure 3B:
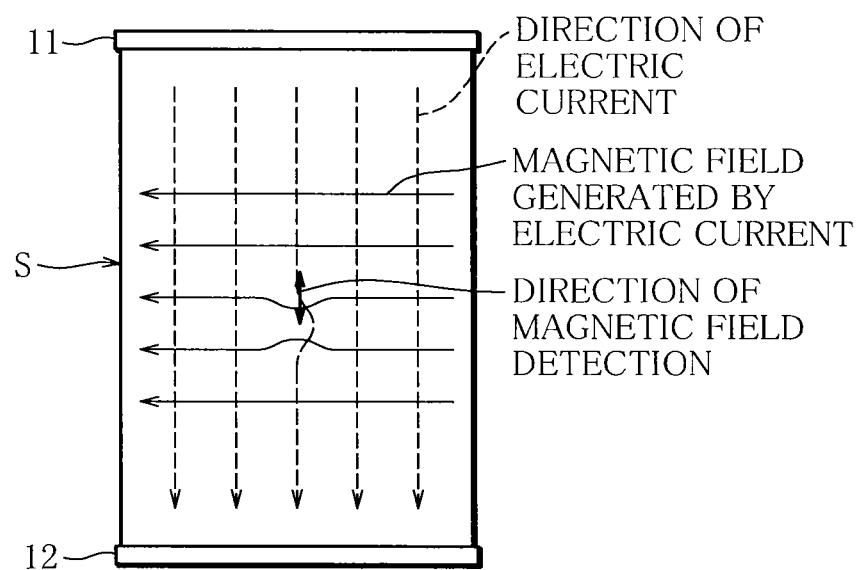
FIG. 3B is an explanatory view illustrating a magnetic field when waviness is present in a case where scanning is performed using the magnetic field sensor shown in FIG. 2A.

In this scanning, any magnetic field change indicating anomalies (disturbance of magnetic fluxes) in the direction of magnetic field detection is not detected, as illustrated in FIG. 3A, if no waviness of the conductive fiber SE is present. If waviness of the conductive fiber SE is present, however, a magnetic field change indicating anomalies in the direction of magnetic field detection is detected, as illustrated in FIG. 3B.

Then, the control unit 6 determines a portion where the magnetic field sensor 3 has detected the magnetic field change as a portion where waviness of the conductive fiber SE of the plurality of prepregs $S_2, S_4, \ldots, S_n$ as targets for verification of the presence or absence of waviness is present.

Accordingly, it is possible to detect waviness of the conductive fiber SE without having to partially or finely cut the test specimen S, and therefore, to grasp the condition of the conductive fiber SE in the test specimen S as a whole.

Hence, demonstrative tests were performed to verify the presence or absence of waviness of the conductive fiber SE in the test specimen S using the fiber waviness detection apparatus 1 according to this embodiment.

At this time, an MI sensor was used as the magnetic field sensor 3. In addition, a specimen prepared by using carbon fiber as conductive fiber which was a base material and using PEI (polyetherimide resin) which was thermoplastic resin as resin serving as a matrix was adopted as the test specimen S. In addition, a specimen for which the presence of waviness in the in-plane direction of carbon fiber was already confirmed by X-ray CT inspection was adopted. Note that the magnetic field sensor 3 is not limited to MI sensors, but a GMR sensor or an FG sensor may also be used.

In addition, an AC current having a frequency of 1 kHz to 10 MHz was used as an electric current to be applied between the pair of electrodes 11 and 12. As test conditions, the current density of the AC current was set to 125 A/m$^2$ or higher and the abovementioned amount of liftoff to 10 mm or smaller.

Here, the reason for setting the frequency of the AC current to 1 kHz to 10 MHz is that frequencies lower than 1 kHz cause a degradation in the performance of waviness detection, whereas frequencies higher than 10 MHz cause an eddy current to concentrate on the front surface Sa or back surface Sb (skin) of the test specimen S due to a so-called skin effect, thus resulting in an failure to detect waviness.

In addition, the reason for setting the current density to 125 A/m$^2$ or higher is that low current densities cause magnetic field signals to become marginal and the performance of waviness detection to degrade. In contrast, overly high current densities cause damage to resin due to heat generation. Accordingly, the upper limit of the current density is individually determined, depending on the type of resin used as a matrix.

If resin serving as a matrix is PEI (polyetherimide resin) which is thermoplastic resin, as in this demonstrative test, the upper limit of the current density is specified as $3.2 \times 10^5$ A/m$^2$ based on the heat resistant temperature of 220° C.

If the matrix is, for example, PEEK (polyether ether ketone resin) which is thermoplastic resin, the upper limit of the current density is specified as $2.1 \times 10^5$ A/m$^2$ based on the heat resistant temperature of 144° C. If the matrix is PIXA (thermoplastic polyimide resin), the upper limit of the current density is specified as $3.4 \times 10^5$ A/m$^2$ based on the heat resistant temperature of 235° C. Alternatively, if the matrix is, for example, epoxy resin which is thermosetting resin, the upper limit of the current density is specified as $1.8 \times 10^5$ A/m$^2$ based on the heat resistant temperature of 120° C. If the matrix is PETI-5, the upper limit of the current density is specified as $4.0 \times 10^5$ A/m$^2$ based on the heat resistant temperature of 270° C. If the matrix is PMR-15, the upper limit of the current density is specified as $5.2 \times 10^5$ A/m$^2$ based on the heat resistant temperature of 340° C.

Yet additionally, the reason for setting the amount of liftoff to 10 mm or smaller is that amounts of liftoff larger than 10 mm cause a degradation in the performance of waviness detection.

Figure 4A:
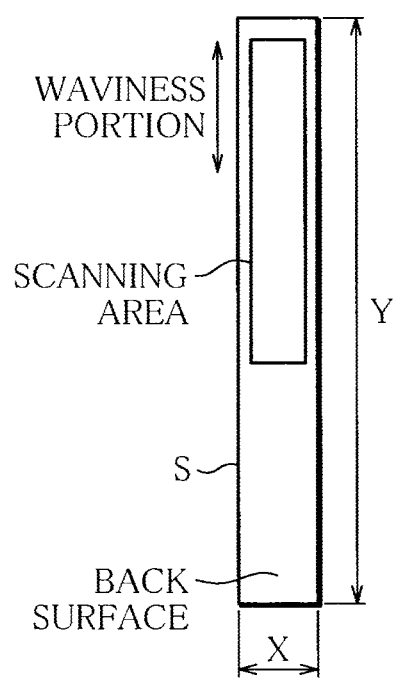
FIG. 4A is an explanatory view of a scanning area when a demonstrative waviness detection test is performed on a test specimen using the fiber waviness detection apparatus for conductive composite materials illustrated in FIG. 1A.

Scanning with the magnetic field sensor 3 was performed by applying an electric current in a Y-axis direction at a scanning rate of 33 mm/s and a scanning pitch of 0.5 mm in the scanning area shown in FIG. 4A, while satisfying the above-described conditions. This scanning brought results shown in the graphs of FIGS. 4B and 4C.

Figure 4B:
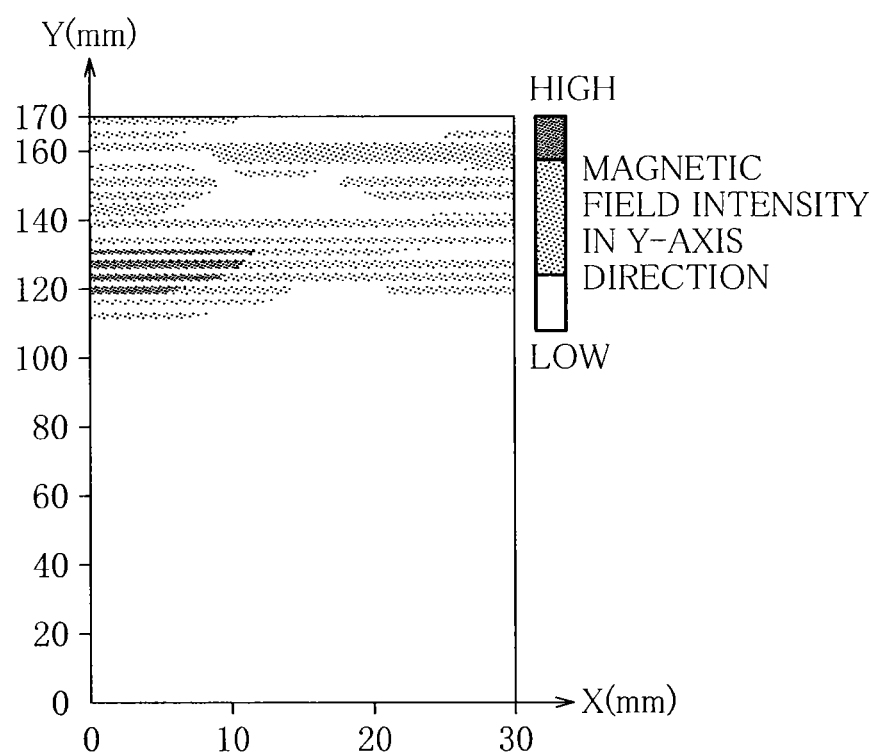
FIG. 4B is a graph illustrating results of waviness detection when scanning the back-surface of a test specimen.
Figure 4C:
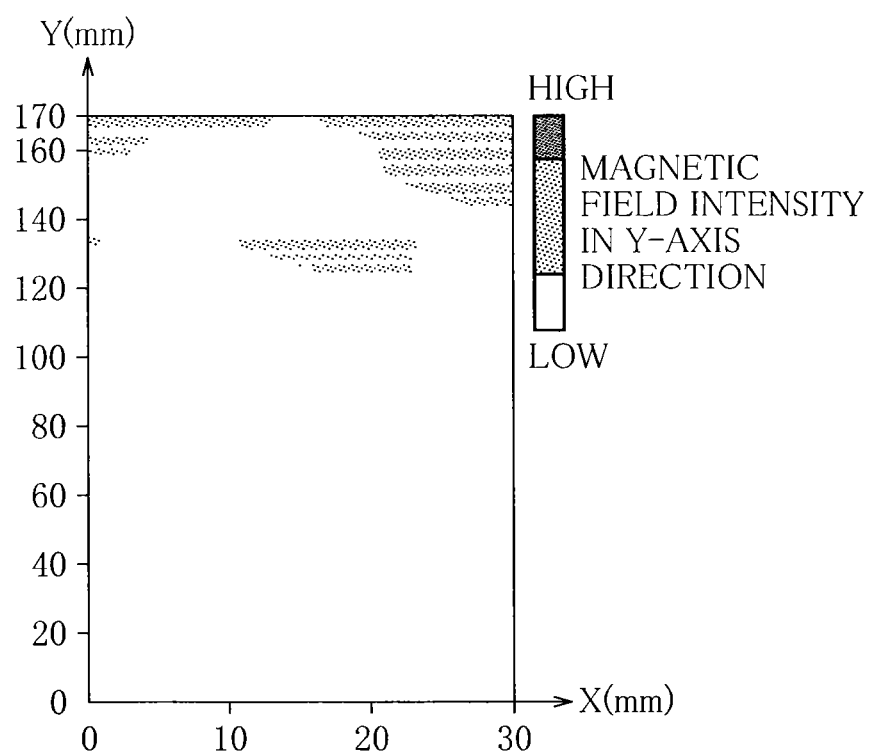
FIG. 4C is a graph illustrating results of waviness detection when scanning the front-surface of a test specimen.

From results of waviness detection illustrated in FIG. 4B in the case of scanning the back surface Sb of the test specimen S and from results of waviness detection illustrated in FIG. 4C in the case of scanning the front surface Sa of the test specimen S, it is understood that magnetic field intensity in the Y-axis direction detected by the scanning of the magnetic field sensor 3 is evidently high in the known waviness portion of the test specimen S.

The present inventors have thus been able to demonstrate that with the fiber waviness detection apparatus 1 according to this embodiment, it is possible to verify the presence or absence of waviness in the in-plane direction of the conductive fiber SE of the test specimen S.

Figure 5A:
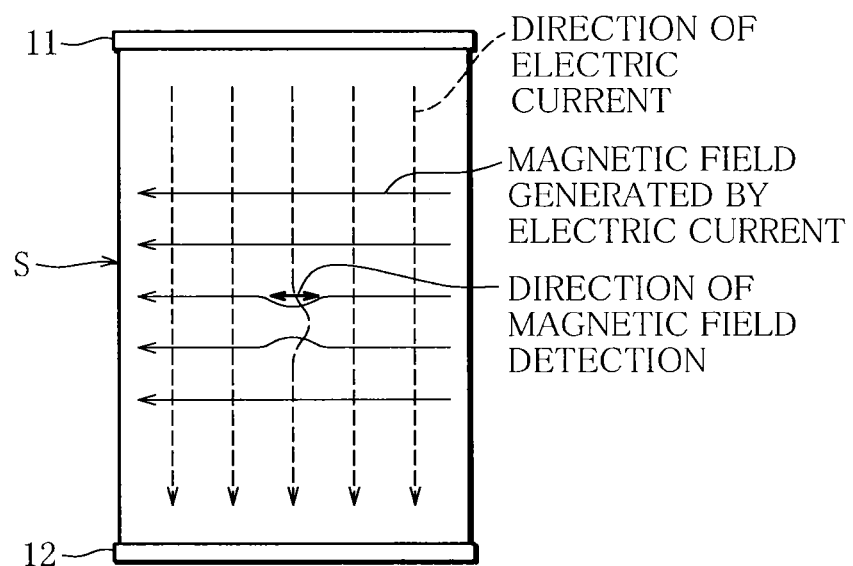
FIG. 5A is an explanatory view illustrating a magnetic field in a case where waviness is present when scanning is performed using the magnetic field sensor of the fiber waviness detection apparatus for conductive composite materials illustrated in FIG. 1A with a magneto-sensitive axis shifted 90°.

In the above-described embodiment, a case is cited in which the magneto-sensitive axis (direction of magnetic field detection) of the magnetic field sensor 3 of the fiber waviness detection apparatus 1 is moved along the direction of the electric current. Scanning is not limited to this method, however. Alternatively, scanning may be performed with the magneto-sensitive axis of the magnetic field sensor 3 shifted 90° (positioned orthogonally to the electric current direction), as illustrated in FIG. 5A.

In addition, in the above-described embodiment, a case is cited in which the magnetic field sensor 3 is used as a magnetic field detection means. The magnetic field detection means is not limited to this sensor, however. A coil may be used as the magnetic field detection means.

Yet additionally, in the above-described embodiment, a case is cited in which the test specimen S fabricated by alternately laminating pluralities of prepregs $(S_1, S_3, \ldots, S_{n-1})$ and $(S_2, S_4, \ldots, S_n)$ different from each other by 90° in fiber orientation direction is shown. Alternatively, the test specimen S may be fabricated by alternately laminating pluralities of prepregs different from each other by, for example, ±45° in fiber orientation direction, or the test specimen S may be fabricated by laminating pluralities of prepregs all of which are the same in fiber orientation direction.

Figure 5B:
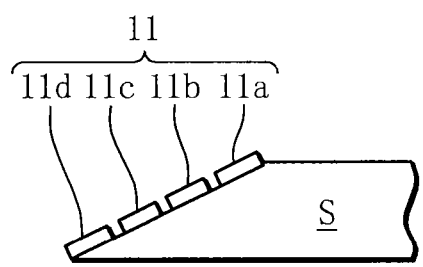
FIG. 5B is a partial side view of a test specimen, illustrating electrodes of a fiber waviness detection apparatus for conductive composite materials according to another embodiment of the present disclosure.

The fiber waviness detection apparatus according to the present disclosure is not limited in configuration to the above-described embodiments. As another configuration, a pair of electrodes 11 (separate electrodes 11a, 11b, 11c and 11d) may be connected to each of the plurality of prepregs as targets for verification of the presence or absence of waviness, as illustrated in FIG. 5B. In this case, it is possible to more accurately detect waviness of the conductive fiber.

A first aspect of the present disclosure is a fiber waviness detection method for conductive composite materials used to detect waviness of the conductive fibers of conductive fiber woven fabrics constituting a conductive composite material composed by laminating a plurality of prepregs prepared by impregnating the conductive fiber woven fabrics with resin, wherein a pair of electrodes is connected to the conductive composite material, in order to apply an electric current to the conductive composite material in the direction of the conductive fibers of the conductive fiber woven fabrics of a plurality of prepregs as targets for verification of the presence or absence of waviness, among the plurality of prepregs constituting the conductive composite material, and then a magnetic field detection means is relatively scanned over the conductive composite material, while applying an electric current between the pair of electrodes, to determine a portion of the conductive composite material where a magnetic field variation is detected by the scanning of the magnetic field detection means as a portion where waviness is present in the conductive fibers of the conductive fiber woven fabrics of the plurality of prepregs as targets for verification of the presence or absence of waviness.

In the fiber waviness detection method for conductive composite materials according to the first aspect of the present disclosure, when an electric current is applied between the pair of electrodes connected to the conductive composite material, the electric current flows in the direction of conductive fibers of conductive fiber woven fabrics of the plurality of prepregs as targets for verification of the presence or absence of waviness. The magnetic field detection means is relatively scanned over the conductive composite material under this condition to determine a portion of the conductive composite material where a magnetic field variation is detected by the magnetic field detection means as a portion where waviness is present in the conductive fibers of the plurality of prepregs as targets for verification of the presence or absence of waviness. It is therefore possible to detect fiber waviness without having to partially or finely cut, for example, a test specimen composed of the conductive composite material.

According to a second aspect of the present disclosure, a pair of electrodes is connected to each of the plurality of prepregs as targets for verification of the presence or absence of waviness, in order to apply an electric current to the conductive composite material in the direction of conductive fibers of conductive fiber woven fabrics of a plurality of prepregs as targets for verification of the presence or absence of waviness, among the plurality of prepregs constituting the conductive composite material.

This configuration makes it possible to more accurately detect fiber waviness.

In addition, one aspect of the fiber waviness detection apparatus according to the present disclosure is a fiber waviness detection apparatus for conductive composite materials used to detect waviness of the conductive fibers of conductive fiber woven fabrics of a conductive composite material composed by laminating a plurality of prepregs prepared by impregnating the conductive fiber woven fabrics with resin, the apparatus comprising a pair of electrodes connected to the conductive composite material, in order to apply an electric current to the conductive composite material in the direction of conductive fibers of the conductive fiber woven fabrics of a plurality of prepregs as targets for verification of the presence or absence of waviness, among the plurality of prepregs constituting the conductive composite material; a current-applying unit that applies an electric current to the conductive composite material through the pair of electrodes; a magnetic field detection means that is relatively scanned over the conductive composite material in a state in which an electric current is applied between the pair of electrodes; and a control unit that determines a portion of the conductive composite material where a magnetic field variation is detected by the scanning of the magnetic field detection means as a portion where waviness of the conductive fibers of the conductive fiber woven fabrics of the plurality of prepregs as targets for verification of the presence or absence of waviness is present.

EXPLANATION OF REFERENCE SIGNS

1: Fiber waviness detection apparatus for conductive composite materials
3: Magnetic field sensor (magnetic field detection means)
4: Current-applying unit
6: Control unit
11, 12: Pair of electrodes
11a, 11b, 11c, 11d: Separate electrodes
S: Test specimen (conductive composite material)
SE: Conductive fiber
SS: Conductive fiber woven fabric
$S_1$ to $S_n$: Prepregs

The invention claimed is:

1. A fiber waviness detection method for conductive composite materials used to detect waviness of conductive fibers of conductive fiber woven fabrics constituting a conductive composite material composed by laminating a plurality of prepregs prepared by impregnating the conductive fiber woven fabrics with resin,
   connecting a pair of electrodes to the conductive composite material, in order to apply an electric current to the conductive composite material in the direction of conductive fibers of the conductive fiber woven fabrics of a plurality of prepregs as targets for verification of the presence or absence of waviness, among the plurality of prepregs constituting the conductive composite material, and
   scanning a magnetic field sensor relatively over the conductive composite material, while applying an electric current between the pair of electrodes, to determine a portion of the conductive composite material where a magnetic field variation is detected by the scanning of the magnetic field sensor as a portion where waviness is present in the conductive fibers of the conductive fiber woven fabrics of the plurality of prepregs as targets for verification of the presence or absence of waviness.

2. The fiber waviness detection method for conductive composite materials according to claim 1, wherein connecting a pair of electrodes to each of the plurality of prepregs as targets for verification of the presence or absence of waviness, in order to apply an electric current to the conductive composite material in the direction of conductive fibers of conductive fiber woven fabrics of the plurality of prepregs as targets for verification of the presence or absence of waviness, among the plurality of prepregs constituting the conductive composite material.

3. A fiber waviness detection apparatus for conductive composite materials used to detect waviness of conductive fibers of conductive fiber woven fabrics constituting a conductive composite material composed by laminating a plurality of prepregs prepared by impregnating the conductive fiber woven fabrics with resin, the apparatus comprising:
   a pair of electrodes connected to the conductive composite material, in order to apply an electric current to the conductive composite material in the direction of conductive fibers of the conductive fiber woven fabrics of a plurality of prepregs as targets for verification of the presence or absence of waviness, among the plurality of prepregs constituting the conductive composite material, an electric current applied to the conductive composite material through the pair of electrodes;

a magnetic field sensor that is relatively scanned over the conductive composite material in a state in which an electric current is applied between the pair of electrodes; and a controller that determines a portion of the conductive composite material where a magnetic field variation is detected by the scanning of the magnetic field sensor as a portion where waviness of the conductive fibers of the conductive fiber woven fabrics of the plurality of prepregs as targets for verification of the presence or absence of waviness is present.

* * * * *